US008901068B2

(12) United States Patent
Smith et al.

(10) Patent No.: US 8,901,068 B2
(45) Date of Patent: Dec. 2, 2014

(54) FUNCTIONAL FRAGRANCE PRECURSOR

(71) Applicant: Colgate-Palmolive Company, Piscataway, NJ (US)

(72) Inventors: Daniel W. Smith, Belvidere, NJ (US); Amjad Farooq, Hillsborough, NJ (US); Donghui Wu, Bridgewater, NJ (US); Marija Heibel, Highland Park, NJ (US); Karen Drehs, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/033,879

(22) Filed: Sep. 23, 2013

(65) Prior Publication Data

US 2014/0056825 A1    Feb. 27, 2014

Related U.S. Application Data

(62) Division of application No. 10/303,287, filed on Nov. 25, 2002, now Pat. No. 8,592,361.

(51) Int. Cl.
| | | |
|---|---|---|
| C11D 3/50 | (2006.01) | |
| A61K 8/35 | (2006.01) | |
| A61Q 13/00 | (2006.01) | |
| C11B 9/00 | (2006.01) | |
| A61K 8/42 | (2006.01) | |
| A61Q 11/00 | (2006.01) | |
| A61K 8/92 | (2006.01) | |

(52) U.S. Cl.
CPC ............. *C11B 9/0007* (2013.01); *A61K 8/42* (2013.01); *A61Q 11/00* (2013.01); *A61Q 13/00* (2013.01); *C11B 9/0003* (2013.01); *C11D 3/507* (2013.01); *C11D 3/50* (2013.01); *A61K 8/925* (2013.01); *C11B 9/0061* (2013.01); *A61K 2800/57* (2013.01)

USPC .......................................................... 512/27

(58) Field of Classification Search
CPC ........................................................ C11D 3/50
USPC .......................................................... 512/27
See application file for complete search history.

(56) References Cited

U.S. PATENT DOCUMENTS 3,208,993 A    9/1965    Fischer et al.
3,563,893 A    2/1971    Doelling et al.
(Continued)

FOREIGN PATENT DOCUMENTS

DE    19948667    4/2001
EP    0012543    6/1980
(Continued)

OTHER PUBLICATIONS

Search and Examination Report from EP03781985 dated Dec. 16, 2009.

(Continued)

*Primary Examiner* — Paul Hyun
(74) *Attorney, Agent, or Firm* — Michael F. Morgan

(57) ABSTRACT

The present invention relates to a class of fragrance precursor compounds comprising one or more of the compounds derived from the reaction of X—OH and an aldehyde or ketone, the fragrance precursor compounds being of the formula X—O—C(R)(R\*)(OR\*\*) wherein R is a $C_{6-24}$ alkyl group, a $C_{6-24}$ aralkyl group or a $C_{6-24}$ alkaryl group; R\* is H or a $C_{6-24}$ alkyl group, a $C_{6-24}$ aralkyl group or a $C_{6-24}$ alkaryl group; R\*\* is H or X; X—O representing a moiety derived from X—OH, and wherein X—OH is a compound selected from the group consisting of surfactants, fabric softeners, softener precursor ester amines, softener precursor amido amines, hair conditioners, skin conditions, saccharides and polymers. In a second aspect it relates to a method of preparing such precursors. Further the invention relates to compositions, comprising the precursor of the invention.

10 Claims, 8 Drawing Sheets

R = Hydrogenated Tallow
n = 2-2.9
Average ~ 2

(56) References Cited

U.S. PATENT DOCUMENTS

| | | |
|---|---|---|
| 3,849,326 A | 11/1974 | Jaggers et al. |
| 4,206,301 A | 6/1980 | Yolles |
| 4,536,315 A | 8/1985 | Ramachandran |
| 4,539,135 A | 9/1985 | Ramachandran |
| 5,188,753 A | 2/1993 | Schmidt et al. |
| 5,232,612 A | 8/1993 | Trinh |
| 5,266,592 A | 11/1993 | Grub et al. |
| 5,336,665 A | 8/1994 | Garner-gray et al. |
| 5,501,806 A | 3/1996 | Farooq et al. |
| 5,506,201 A | 4/1996 | McDermott et al. |
| 5,531,910 A | 7/1996 | Severns et al. |
| 5,622,926 A | 4/1997 | Schade et al. |
| 5,626,852 A | 5/1997 | Suffis et al. |
| 5,627,151 A | 5/1997 | Detering et al. |
| 5,648,328 A | 7/1997 | Angell et al. |
| 5,663,406 A | 9/1997 | King et al. |
| 5,691,303 A | 11/1997 | Pan et al. |
| 5,753,264 A | 5/1998 | Magdassi et al. |
| 6,083,892 A | 7/2000 | Severns et al. |
| 6,093,691 A | 7/2000 | Sivik et al. |
| 6,096,704 A | 8/2000 | Bryant et al. |
| 6,100,233 A | 8/2000 | Sivik et al. |
| 6,156,710 A | 12/2000 | Sivik et al. |
| 6,277,796 B1 | 8/2001 | Sivik et al. |
| 6,306,818 B1 | 10/2001 | Anderson et al. |
| 6,395,695 B1 | 5/2002 | Sivik |
| 6,492,563 B2 | 12/2002 | Gautschi et al. |
| 6,861,402 B1 | 3/2005 | Miracle |

FOREIGN PATENT DOCUMENTS

| | | |
|---|---|---|
| EP | 423894 | 4/1991 |
| EP | 684301 | 11/1995 |
| EP | 760243 | 3/1997 |
| EP | 0905115 | 3/1999 |
| EP | 1096004 | 5/2001 |
| GB | 2313379 | 11/1997 |
| GB | 2359750 | 9/2001 |
| WO | WO 95/22311 | 8/1995 |
| WO | WO 96/02625 | 2/1996 |
| WO | WO 96/04937 | 2/1996 |
| WO | WO 96/12785 | 5/1996 |
| WO | WO 97/06234 | 2/1997 |
| WO | WO 97/30687 | 8/1997 |
| WO | WO 97/30688 | 8/1997 |
| WO | WO 97/30689 | 8/1997 |
| WO | WO 97/31094 | 8/1997 |
| WO | WO 97/34578 | 9/1997 |
| WO | WO 97/34986 | 9/1997 |
| WO | WO 97/48374 | 12/1997 |
| WO | WO 97/48375 | 12/1997 |
| WO | WO 97/48378 | 12/1997 |
| WO | WO 98/27192 | 6/1998 |
| WO | WO 98/45245 | 10/1998 |
| WO | WO 98/47478 | 10/1998 |
| WO | WO 98/47995 | 10/1998 |
| WO | WO 99/00347 | 1/1999 |
| WO | WO 99/16740 | 4/1999 |
| WO | WO 00/00580 | 1/2000 |
| WO | WO 00/11134 | 3/2000 |
| WO | WO 00/57400 | 9/2000 |
| WO | WO 00/72816 | 12/2000 |
| WO | WO 02/055648 | 7/2002 |

OTHER PUBLICATIONS

"PEG-40 stearate ED—Ash Michael; Ash Irene", Jan. 1, 2000, Handbook of Industrial Surfactants, Synapse Information Resources, Inc., Endicott, NY, p. 1299. XP002696395, ISBN:978-1-890595-21-0.

|  | Day 1 | Day 5 |
|---|---|---|
| C8 Aldehyde | 4,359,202 | 7,148,940 |
| C9 Aldehyde | 26,305,887 | 58,252,609 |
| C10 Aldehyde | 41,464,339 | 41,222,877 |

FIG. 2

FUNCTIONAL FRAGRANCE PRECURSOR

CROSS REFERENCE TO RELATED APPLICATIONS

This application is a divisional application of Ser. No. 10/303,287, filed on 25 Nov. 2002, which is incorporated herein by reference in its entirety.

TECHNICAL FIELD

The present invention relates to a class of compounds, and especially a group of fragrance precursor compounds which are used for creating a fragrance effect, preferably on surfaces such as fibers, skin, hair and hard surfaces. More specifically, the invention relates to a group of fragrance precursor compounds that break down on the above outlined surfaces, and as a result of this release perfume. In preferred embodiments the invention relates to certain hemiacetal and acetal compounds. Since the perfume or fragrance is only released when the compounds of the invention are broken down, the compounds of the invention are capable of providing a long-lasting fragrance effect. That is, the compounds of the present invention provide for a sustained release of fragrances.

In a further aspect, the present invention relates to a process for preparing these precursor compounds. Fragrance precursor compounds consist of fragrance raw materials and functional compounds such as surfactants, polymers etc., which provide benefits such as surface protection, surface conditioning, and/or surface cleaning.

In addition, the present invention relates to compositions comprising the compounds of the invention, and to fragrance raw material delivery systems which provide extended fragrance benefits.

BACKGROUND OF THE INVENTION

In WO-00/72816, fragrance delivery systems are described which comprise pro-fragrances or pro-accords selected from at least two of the following: (i) aldehyde and ketone releasing pro-fragrances, which pro-fragrances comprise inter alia and preferably oxazolidines; (ii) β-amino pro-fragrances; and (iii) orthoester pro-accords. The pro-fragrances described are capable of delivering fragrance raw material aldehydes and ketones to especially the human skin. More in detail, said international patent application is based on the finding that certain aldehyde fragrance raw materials, such as para-t-bucinal, cymal and lillial can be controllably released from particular heterocyclic pro-fragrances to especially the skin.

In laundry products, such as fabric softeners or detergents, generally perfume additives are present which make the said products more aesthetically pleasing to the consumers. The product should not only smell pleasantly and in that way add to the purchase perception, but also impart a pleasant and preferably long, lasting fragrance to the fibers or fabrics treated therewith. One of the problems the person skilled in the art is confronted with is that the amount of perfume carryover is rather marginal; much fragrance is lost during washing and disappears down the drain. It would be very desirable to find ways of more effectively delivering perfume or fragrances to fibers, fabrics and textiles and to achieve the fragrance effect for a longer period of time.

Colgate-Palmolive application WO 02/057400 describes a water soluble cross-linked cationic polymer derived from the polymerisation of from 5 to 100 mole percent of a cationic vinyl addition monomer, from 0 to 95 mole percent of acrylamide, and from 70 to 300 ppm of a difunctional vinyl addition monomer cross-linking agent which enhances fragrance delivery from a fabric softening composition to the fabric to be softened.

In copending Colgate-Palmolive U.S. application Ser. No. 09/893,117, filed Jun. 27, 2001, there is described a fabric care composition comprising a cationic softening compound; a non-confined fragrance oil; and at least one fabric or skin beneficiating ingredient such as a fragrance oil, contained within pressure sensitive microcapsules to provide enhanced delivery of such beneficiating ingredient to the fabric.

OBJECTIVES OF THE PRESENT INVENTION

The first objective of the present invention is to provide alternative fragrances precursors or pro-fragrances.

It is another objective to provide a more efficient delivery system of fragrance or perfume to surfaces.

It is a further objective to provide functional fragrance precursor compounds that impart long lasting fragrance benefits, especially to fiber containing materials, such as fabrics and laundry.

Moreover, it is an objective of the present invention to provide a controlled or sustained release system releasing fragrance for a longer period of time.

Yet a further objective is to provide consumer product compositions which are capable to provide sustained release of fragrance.

Other objectives will become apparent from reading the following description and are especially obtained for laundry products, personal care products, hard surface care products, oral products and so on.

SUMMARY OF THE INVENTION

According to the present invention a class of chemical compounds, and especially a class of fragrance precursor compounds has been found, which form the basis of products and methods which meet at least a number of the above-identified objectives.

More in particular, the present invention provides fragrance precursor compounds that are capable of breakdown under ambient conditions and that are the reaction product of a reaction between a hydroxyl compound, X—OH, and an aldehyde or a ketone. More in detail, the invention relates to a fragrance precursor compound comprising one or more of the compounds derived from the reaction of X—OH and an aldehyde or ketone, said fragrance precursor compounds being of the formula X—O—C(R)(R*)(OR**) wherein R is a $C_{6-24}$ alkyl group, a $C_{6-24}$ aralkyl group or a $C_{6-24}$ alkaryl group; R* is H or a $C_{6-24}$ alkyl group, a $C_{6-24}$ aralkyl group or a $C_{6-24}$ alkaryl group; R** is H or X; X—O representing a moiety derived from X—OH, and wherein X—OH is a compound selected from the group consisting of surfactants, fabric softeners, softener precursor ester amines, softener precursor amido amines, hair conditioners, skin conditions, saccharides and polymers.

In preferred embodiments X—OH is of the following structure:

I.

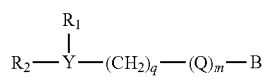

wherein $R_1$ and $R_2$ are each independently, H or:
(a) $C_1$-$C_{22}$ alkylenecarboxy moiety having the formula —$(CH_2)_e R_3$ wherein $R_3$ is —$NHCOR_4$; or —$OCOR_4$; or —$NR_5COR_4$; and wherein $R_4$ and $R_5$ are each independently $C_1$-$C_{22}$ alkyl or alkenyl; and e is an integer from 1 to 22; or
(b) $C_1$-$C_{22}$ linear or branched alkyl; or
(c) $C_1$-$C_{22}$ linear or branched alkenyl; or
(d) $C_2$-$C_{22}$ substituted or unsubstituted alkylenoxy; or
(e) $C_3$-$C_{22}$ substituted or unsubstituted alkylenoxy alkyl; or
(f) $C_6$-$C_{22}$ substituted or unsubstituted aryloxy; or
(g) $C_7$-$C_{22}$ substituted or unsubstituted alkylenearyl; or
(h) $C_7$-$C_{22}$ substituted or unsubstituted alkyleneoxyary; or
(i) $C_7$-$C_{22}$ oxyalkylenearyl; or
(j) an anionic unit having the formula:

wherein $R_6$ is —$SO_3M$, —$OSO_3M$, —$PO_3M$, —$OPO_3M$, Cl or mixtures thereof,
wherein M is hydrogen, or one or more salt forming cations sufficient to satisfy charge balance, or mixtures thereof;
y is an integer from 1 to about 22; or
(k) a mixture comprising at least two of (a) through (j); and
(l) q is an integer from 0 to about 22; m is an integer from 0 to about 22; Q is $(CH_2)_m$ or $(CH_2CHR_7O)$; $R_7$ is independently hydrogen, methyl, ethyl, propyl or benzyl; B is H or OH; and Y is $CR_1$ or N.

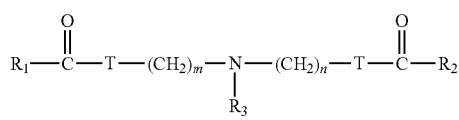

II.

wherein $R_1$ and $R_2$, independently, represent $C_{12}$ to $C_{30}$ aliphatic hydrocarbon groups,
$R_3$ represents $(CH_2CH_2O)_pH$, $CH_3$, or H; T represents NH; n is an integer from 1 to 5;
m is an integer from 1 to 5 and p is an integer from 1 to 10.
III.
wherein $R_1$ is H or:

 III.

(a) $C_1$-$C_{22}$ alkenecarboxy moiety having the formula: —$(CH_2)_e R_3$ wherein $R_3$ is —$NHCOR_4$; or —$OCOR_4$; or —$NR_5COR_4$; and wherein $R_4$ and $R_5$ are each independently $C_1$-$C_{22}$ akyl or alkenyl; and e is an integer from 1 to 22; or
(b) $C_1$-$C_{22}$ linear or branched alkyl; or
(c) $C_1$-$C_{22}$ linear or branched alkenyl; or
(d) $C_2$-$C_{22}$ substituted or unsubstituted alkylenoxy; or
(e) $C_3$-$C_{22}$ substituted or unsubstituted alkylenoxy alkyl; or
(f) $C_6$-$C_{22}$ substituted or substituted aryloxy; or
(g) $C_7$-$C_{22}$ substituted or substituted alkylenearyl; or
(h) $C_7$-$C_{22}$ substituted or substituted alkyleneoxyaryl; or
(i) $C_7$-$C_{22}$ oxyalkylenearyl; or
(j) an anionic unit having the formula:

wherein $R_6$ is —$SO_3M$, —$OSO_3M$, —$PO_3M$, —$OPO_3M$, Cl or mixtures thereof,
wherein M is hydrogen, or one or more salt forming canons sufficient to satisfy charge balance, or mixtures thereof; y is an integer from 1 to about 22; and (k) a mixture comprising at least two of (a) through (j); and
q is an integer from 0 to about 22, m is an integer from 0 to about 22; Q is $(CH_2)_m$ or $(CH_2CHR_7O)$; $R_7$ is independently hydrogen, methyl, ethyl, propyl or benzyl;
B is H or OH; and Y is O or S.

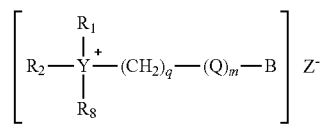

IV.

wherein $R_1$ and $R_2$ are each independently, H or:
(a) $C_1$-$C_{22}$ alkenecarboxy moiety having the formula: —$(CH_2)_e R_3$ wherein $R_3$ is —$NHCOR_4$; or —$OCOR_4$; or —$NR_5COR_4$; and wherein $R_4$ and $R_5$ are each independently $C_1$-$C_{22}$ akyl or alkenyl; and e is an integer from 1 to 22; or
(b) $C_1$-$C_{22}$ linear or branched alkyl; or
(c) $C_1$-$C_{22}$ linear or branched alkenyl; or
(d) $C_2$-$C_{22}$ substituted or unsubstituted alkylenoxy; or
(e) $C_3$-$C_{22}$ substituted or unsubstituted alkylenoxy alkyl; or
(f) $C_6$-$C_{22}$ substituted or substituted aryloxy; or
(g) $C_7$-$C_{22}$ substituted or unsubstituted alkylenearyl; or
(h) $C_7$-$C_{22}$ substituted or unsubstituted alkyleneoxyaryl; or
(i) $C_7$-$C_{22}$ oxyalkylenearyl; or
(j) an anionic unit having the formula:

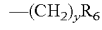

wherein $R_6$ is —$SO_3M$, —$OSO_3M$, —$OPO_3M$, Cl or mixtures thereof,
wherein M is hydrogen, or one or more salt forming cations sufficient to satisfy charge balance, or mixtures thereof; $R_6$ may also be chloride; y is an integer from about 1 to about 22; and
(k) a mixture comprising at least two of (a) through (j); and
q is an integer from 0 to about 22; m is an integer from 0 to about 22; Q is $(CH_2)_m$ or $(CH_2CHR_7O)$; $R_7$ is independently hydrogen, methyl, ethyl, propyl or benzyl;
and mixtures thereof; B is H or OH; Y is C or N; $R_8$ is H or $C_1$-$C_4$ alkyl; $Z^-$ is a counter anion, and preferably chloride, or methyl sulfate.

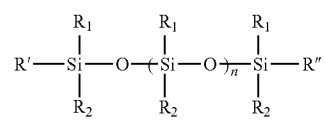

V.

wherein $R_1$ and $R_2$ are as defined in I; R' and R" are each independently OH or $R_1$ with the proviso that at least one of R' and R" is OH.

In a second aspect, the present invention relates to a process for preparing the products of the invention, comprising reacting an aldehyde and or ketone and a compound X—OH. X—OH is defined as above.

In a third aspect, the present invention relates to an aqueous composition for fragrance delivery comprising one or more of the reaction products according to the invention. Preferably, said composition of comprises a fabric softener.

BRIEF DESCRIPTION OF THE DRAWINGS

In the drawings,

FIG. 2 shows the release of fragrance from fabric treated with fabric softener containing the fragrance precursor compounds of the present invention after 1 and after 5 days, for a $C_8$, $C_9$ and $C_{10}$ aldehydes by Solid Phase Micro Extraction GC/MS.

DETAILED DESCRIPTION OF THE INVENTION

Figure 1:
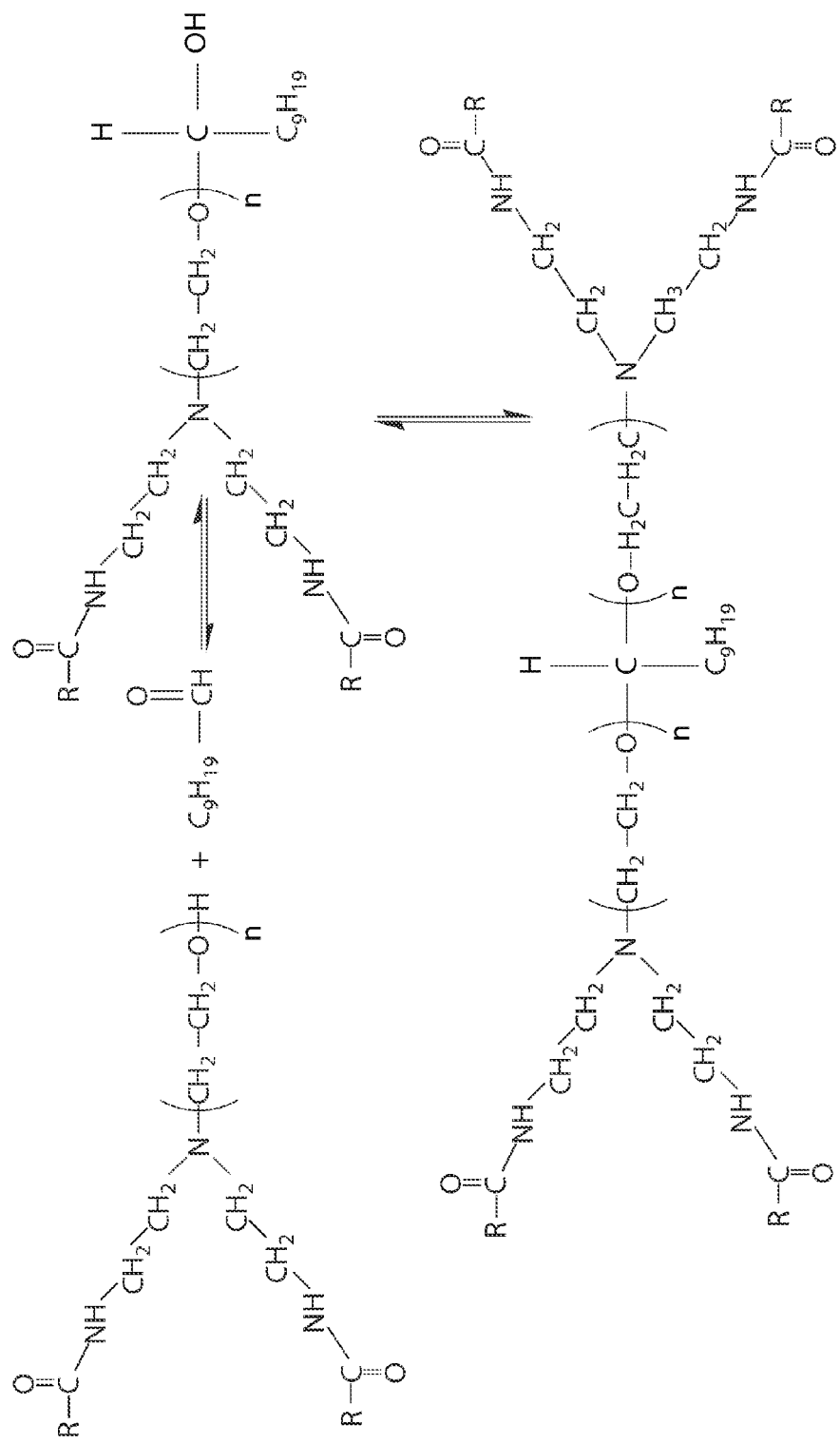
FIG. 1 shows the reaction between a difatty amido amine and a $C_{10}$ aldehyde.
Figure 3:
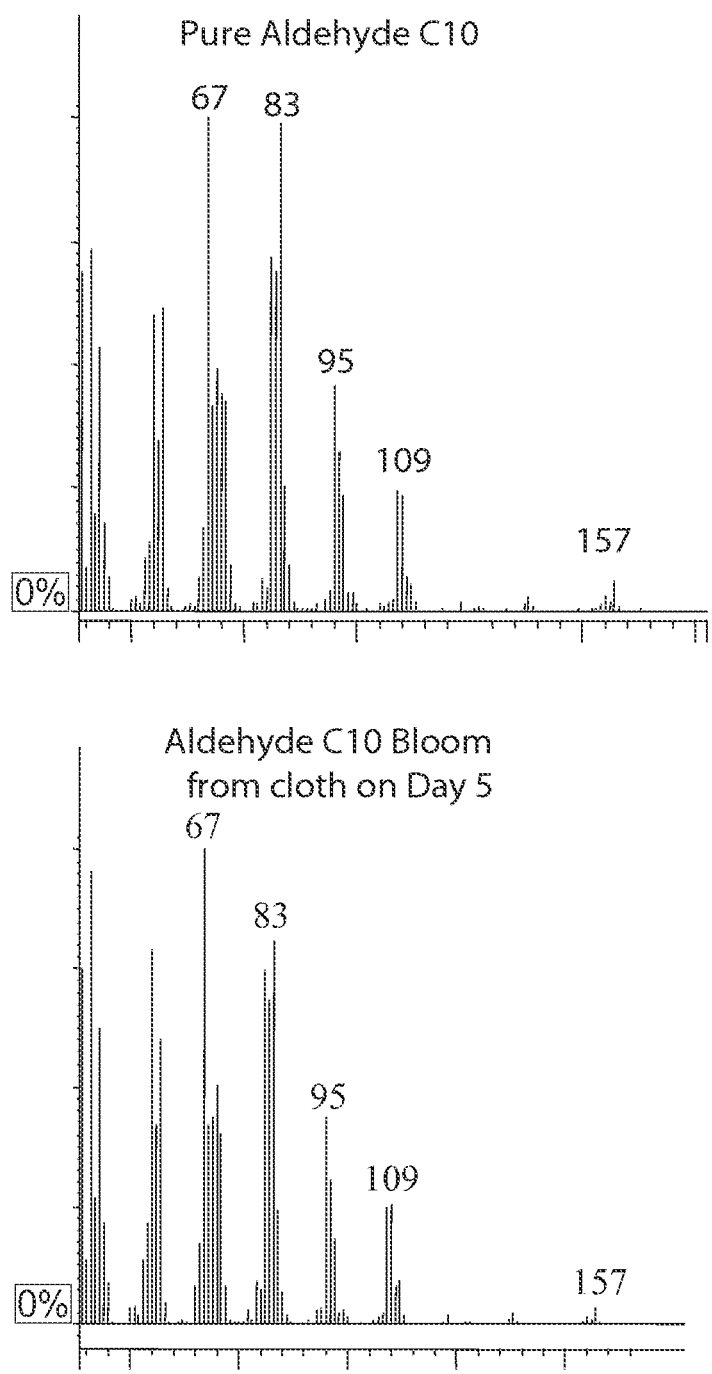
FIG. 3 shows a GC/MS spectrum of pure $C_{10}$ aldehyde, and the compound released from cloth treated with a fragrance precursor compound based on $C_{10}$ aldehyde and Varisoft 510.
Figure 4A:
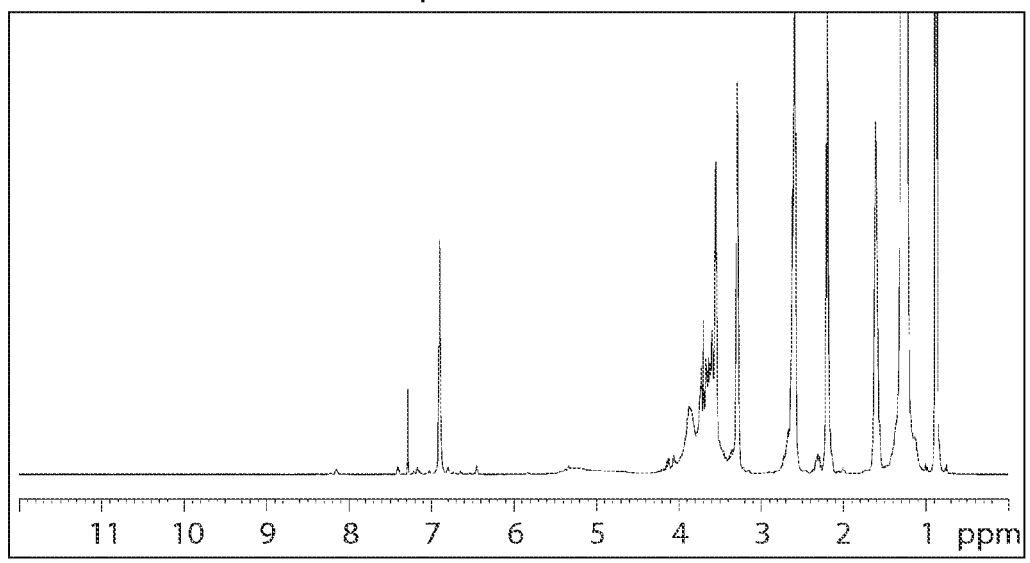
FIGS. 4a-4d show the proton-NMR spectra and the $^{13}$C-NMR spectra of Varisoft 510 and Varisoft 510 reacted with $C_{10}$ aldehyde.
Figure 4B:
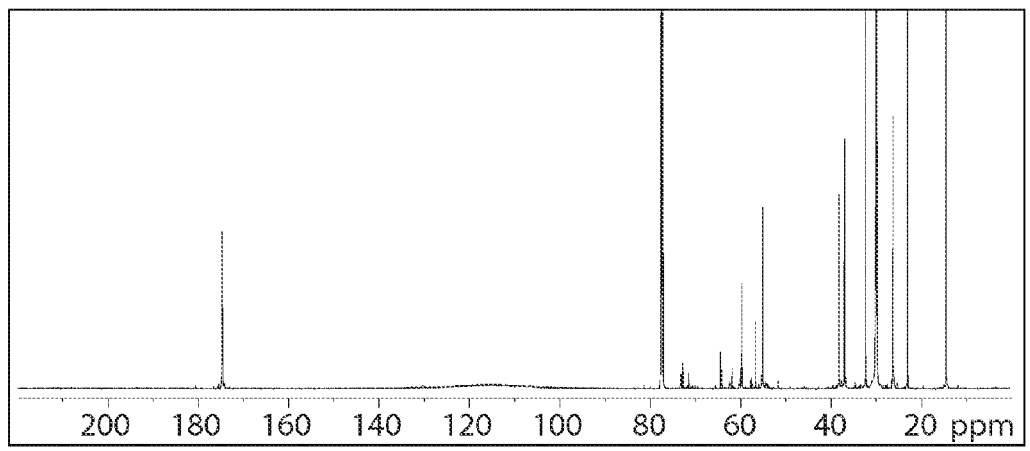
Figure 4C:
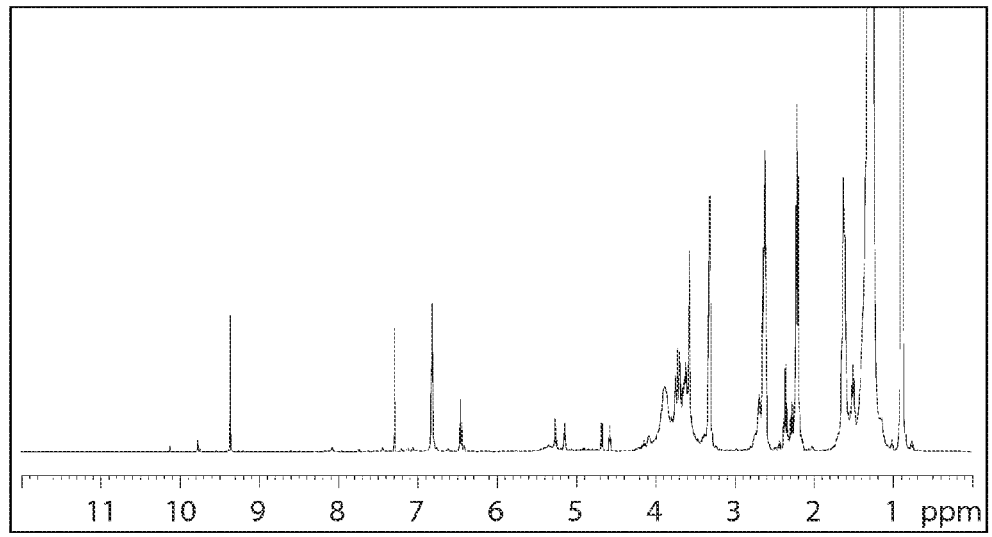
Figure 4D:
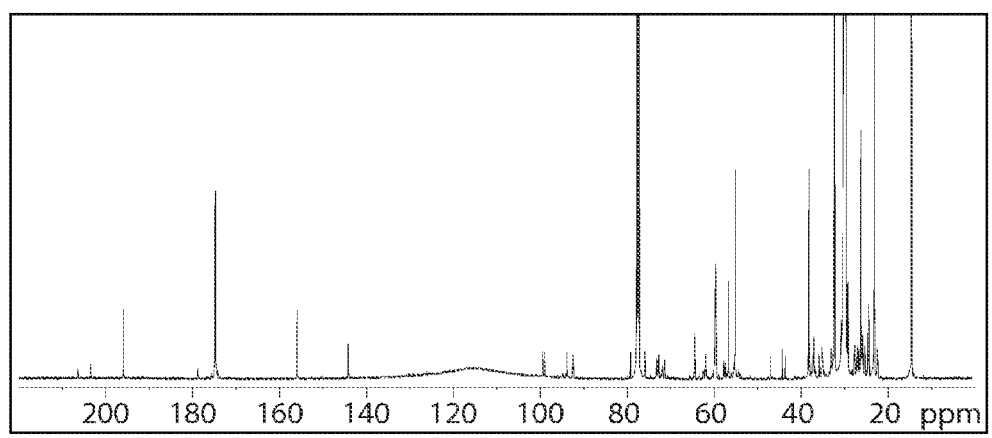

As mentioned herein-above, the present invention relates to the reaction product of a reaction between X—OH and an aldehyde or a ketone. In the aldehyde or ketone starting compounds of this reaction, the $C_{6-24}$ alkyl moiety encompasses linear and branched alkyl groups which can have one or more unsaturations. Such groups can be substituted with substituents which do not adversely affect the fragrance activity of the aldehyde or ketones. Examples of such substituents encompass F, Cl and OH.

The $C_{6-24}$ alkaryl and aralkyl moiety can also be branched and contain substituents that do not adversely affect the fragrance properties.

In a more preferred embodiment, X—OH preferably is of the following structure:

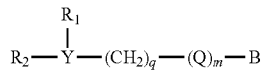

wherein $R_1$ and $R_2$ are each independently, H or:

(a) $C_1$-$C_{22}$ alkylenecarboxy moiety having the formula —$(CH_2)_eR_3$ wherein $R_3$ is —$NHCOR_4$; or —$OCOR_4$; or —$NR_5COR_4$; and wherein $R_4$ and $R_5$ are each independently $C_1$-$C_{22}$ akyl or alkenyl; and e is an integer from 1 to 22; or
(b) $C_1$-$C_{22}$ linear or branched alkyl; or
(c) $C_1$-$C_{22}$ linear or branched alkenyl; or
(d) $C_2$-$C_{22}$ substituted or unsubstituted alkylenoxy; or
(e) $C_3$-$C_{22}$ substituted or unsubstituted alkylenoxy alkyl; or
(f) $C_6$-$C_{22}$ substituted or unsubstituted aryloxy; or
(g) $C_7$-$C_{22}$ substituted or unsubstituted alkylenearyl; or
(h) $C_7$-$C_{22}$ substituted or unsubstituted alkyleneoxyaryl; or
(i) $C_7$-$C_{22}$ oxyalkylenearyl; or
(j) an anionic unit having the formula:

wherein $R_6$ is —$SO_3M$, —$OSO_3M$, —$PO_3M$, —$OPO_3M$, Cl or mixtures thereof, wherein M is hydrogen, or one or more salt forming cations sufficient to satisfy charge balance, or mixtures thereof; y is an integer from 1 to about 22; or (k) a mixture comprising at least two of (a) through (j); and q is an integer from 0 to about 22; m is an integer from 0 to about 22; Q is $(CH_2)_m$ or $(CH_2CHR_7O)$; $R_7$ is independently hydrogen, methyl, ethyl, propyl or benzyl; B is H or OH; and Y is $CR_1$ or N.

The aldehydes useful in the present invention can be one or more of, but is not limited to the following group of aldehydes:

(a) Phenylacetaldehyde; or
(b) p-methyl phenylacetaldehyde; or
(c) p-isopropyl phenylacetaldehyde; or
(d) methylnonyl acetaldehyde; or
(e) phenylpropanal; or
(f) 3-(4-t-butylphenyl)-2-methyl propanal; or
(g) 3-(4-t-butylphenyl)-propanal; or
(h) 3-(4-methoxyphenyl)-2-methylpropanal; or
(i) 3(4-isopropylphenyl)-2-methylpropanal; or
(j) 3-(3,4-methylenedioxyphenyl)-2-methylpropanal; or
(k) 3-(4-ethylphenyl)-2,2dimethylpropanal; or
(l) phenylbutanal; or
(m) 3-methyl-5-phenylpentanal; or
(n) hexanal; or
(o) trans-2-hexenal; or
(p) cis-hex-3-enal; or
(q) heptanal; or
(r) cis-4-heptenal; or
(s) 2-ethyl-2-heptenal; or
(t) 2,6-dimethylpropanal; or
(u) 2,4-heptadienal; or
(v) octanal; or
(w) 2-octenal; or
(x) 3,7-dimethyloctanal; or
(y) 3,7-dimethyl-2,6-octadien-1-al; or
(z) 3,7-dimethyl-1,6-octadien-3-al; or
(aa) 3,7-dimethyl-6-octenal; or
(bb) 3,7-dimethyl-7-hydroxyoctan-1-al; or
(cc) nonanal; or
(dd) 6-nonenal; or
(ee) 2,4-nonadienal; or
(ff) 2,6-nonadienal; or
(gg) decanal; or
(hh) 2-methyl decanal; or
(ii) 4-decenal; or
(jj) 9-decenal; or
(kk) 2,4-decadienal; or
(ll) undecanal; or
(mm) 2-methyldecanal; or
(nn) 2-methylundecanal; or
(oo) 2,6,10-trimethyl-9-undecenal; or
(pp) undec-10-enyl aldehyde; or
(qq) undec-8-enanal; or
(rr) dodecanal; or
(ss) tridecanal; or
(tt) tetradecanal; or
(uu) anisaldehyde; or
(vv) bourgenonal; or
(ww) cinnamic aldehyde; or
(xx) α-amylcinnam-aldehyde; or
(yy) α-hexyl cinnamaldehyde; or
(zz) methoxy cinnamaldehyde; or
(aaa) citronellal; or
(bbb) hydroxy-citronella; or
(ccc) isocyclocitral; or
(ddd) citronellyl oxyacet-aldehyde; or
(eee) cortexaldehyde; or
(fff) cumminic aldehyde; or
(ggg) cyclamem aldehyde; or (hhh) florhydral; or
(iii) heliotropin; or
(jjj) hydrotropic aldehyde; or
(kkk) lilial; or
(lll) vanillin; or
(mmm) ethyl vanillin; or
(nnn) benzaldehyde; or
(ooo) p-methyl benzaldehyde; or
(ppp) 3,4-dimethoxybenzaldehyde; or
(qqq) 3- and 4-(4-hydroxy-4-methyl-pentyl)-3-cyclobexene-1-caroxaldehyde; or
(rrr) 2,4-dimethyl-3-cyclohexene-1-carboxaldehyde; or
(sss) 1-methyl-3-4-methylpentyl-3-cyclohexencarboxyaldehyde; and
(ttt) p-methylphenoxyacetaldehyde When an aldehyde is used the precursor of the invention is an acetal or hemiacetal.

The ketones useful in the present invention can be one or more of, but is not limited to the group of following ketones:
(a) alpha-damascone; or
(b) beta-damascone; or
(c) delta-damascone; or
(d) beta-damascenone; or
(e) muscone; or
(f) 6,7-dihydro-1,1,2,3,3-pentamethyl-4(5H)-indanone; or
(g) cashmeran; or
(h) cis-jasmone; or
(i) dihydrojasmone; or
(j) alpha-ionone; or
(k) beta-ionone; or
(l) dihydro-beta-ionone; or
(m) gamma-methyl ionone; or
(n) alpha-iso-methyl onone; or
(o) 4-(3,4-methylenedioxyphenyl)butan-2-one; or
(p) 4-(4-ydroxyphenyl)butan-2-one; or
(q) methyl beta-naphthyl ketone; or
(r) methyl cedryl ketone; or
(s) 6-acetyl-1,1,2,4,4,7-hexamethyltetralin (tonalid); or
(t) 1-carvone; or
(u) 5-cyclohexadecen-1-one; or
(v) acetophenone; or
(w) decatone; or
(x) 2-[2-(4-3-cyclohexenyl-1-yl)propyl]cyclopentan-2-one; or
(y) 2-sec-butylcyclohexanone; or
(z) beta-dihydro ionone; or
(aa) allyl ionone; or
(bb) alpha-irone; or
(cc) alpha-cetone; or
(dd) alpha-irisone; or
(ee) acetanisole; or
(ff) geranyl acetone; or
(gg) 1-(2-methl-5-isopropyl-2-cyclohexenyl)-1-propanone; or
(hh) acetyl diisoamylene; or
(ii) methyl cyclocitrone; or
(jj) 4-t-pentyl cyclohexanone; or
(kk) p-t-butylcelohexanone; or
(ll) o-t-butyloyelohexanone; or
(mm) ethyl amyl ketone; or
(nn) ethyl pentyl ketone; or
(oo) menthone; or
(pp) methyl-7,3-dihydro-2H-1,5-benzodioxepine-3-one; or
(qq) fenchone; or
(rr) methyl naphthyl ketone; or
(ss) propyl naphthy ketone; and
(tt) methyl hydroxynaphthyl ketone The fragrance precursor compounds of the invention were found to act as source for long lasting fragrance benefits, especially when applied to on surfaces such as fibers, skin, hair and hard surfaces, especially to fabrics and laundry. More specifically, the invention relates to fragrance precursor compounds that break down on surfaces such as fibers, skin, hair and hard surfaces, especially to fabrics and laundry, and as a result of this release perfume.

Since the perfume or fragrance is only released when the compounds of the invention are broken down, the compounds of the invention are capable of providing a long-lasting fragrance effect. That is, the compounds of the present invention provide for a sustained release of fragrances.

In accordance with the present invention there is a balance between the degree of breakdown of the fragrance precursor compounds to form the fragrance and the intensity of the fragrance. The intensity of the fragrance is substantially based on the fragrance formed.

To guarantee also the release of fragrance after a few days such as after 5 and preferably after 7 days, the fragrance must be released by a controlled breakdown of the fragrance precursor compounds of the invention. That is, the equilibrium between the fragrance precursor compounds and the components including the fragrance must preferably be such that sufficient fragrance is released during a number of days. This equilibrium depends on the type of aldehyde and or ketone and the nature of compound X—OH.

In another embodiment of the present invention, the fragrance precursor compound of the invention is derived from a compound X—OH, selected from the group consisting of polyalkylene glycol, polyalkylene glycol ester and polysaccharide. Preferably, the polyalkylene glycol or the ester thereof are based on polyethylene glycol, polypropylene glycol and poly(ethylene/propylene) glycol.

The fragrance precursor compounds of the present invention are especially aimed to be incorporated in compositions to treat surfaces such as fibers, skin, hair and hard surfaces, especially to fabrics and laundry. From that perspective, it would be highly desirable to have available compounds which not only are compatible with compositions used to treat such materials, but additionally would have properties useful in such compositions. In this respect, in specifically preferred embodiments, the present invention relates to fragrance precursor compounds of the type described hereinabove, wherein X—OH is a surfactant described hereinabove as I. The preferred structure is of the formula $(R_1—(CH_2)_z)_x—N—(CH_2)_y—OH$, wherein $R_1$, independently, is selected from the group consisting of a fatty amido amine moiety of the formula AlkC(O)NH—, a moiety having the formula AlkC(O)O, a moiety having the formula Alk-O—, wherein Alk is a linear or branched $C_2$-$C_{24}$ alkyl or alkylene group, optionally substituted with one or more hydroxyl groups, nitro groups, amine groups, and/or halogen atoms, or represents a CHOH—R group. z and y, independently, are integers having a value between 0 and 10, preferably between 0 and 5, more preferably between 1 and 3;
x represents 2 or 3.

These fragrance precursor compounds are for instance based on fatty or di fatty amido amines, which in themselves have fabric softening properties. Examples of such fatty amido amines are for instance the fabric softeners sold under the trade name Varisoft, such as Varisoft 510 (ex Goldschmidt, Germany) as mentioned in U.S. Pat. No. 5,501,806. As will follow from the examples herein-below the reaction product between a di fatty amido amine (Varisoft 510) and $C_{8-12}$ aldehydes give pro-fragrances that give continuous release of the aldehydes until after more than week.

The fragrance precursor compounds of the invention can be obtained by reacting an aldehyde and or ketone fragrance and a compound X—OH; X—OH is selected from the group consisting of surfactants, fabric softeners, softener precursor ester amines or amido amines, hair and skin conditioners and polymers. This forms a further aspect of the present invention.

In fact, the formation of a acetal, hemiacetal, and or a ketal involves a compound comprising at least one nucleophilic free —OH group and an aldehyde and or ketone. This reaction is known per se. Preferably, this reaction is carried out in an aqueous solution in the presence of an acid or a catalyst.

In FIG. 1, the reaction between an amido amine and a $C_{10}$ aldehyde is shown as an example. An example of the amido amine starting compound is Varisoft 510. The products obtained from this reaction can very suitably be incorporated in a product formula such as a rinse cycle fabric softener, and from said formula be delivered to a surface to give a long lasting fragrance.

Dependent on the number of free hydroxyl groups, one or more aldehyde and or ketone molecules can be coupled to the XOH molecule. This makes that the capacity of fragrance to be released can be controlled to some degree.

In yet a further aspect, the present invention relates to an aqueous composition for fragrance delivery comprising one or more fragrance precursor compounds according to the invention. Preferable said aqueous composition is a fabric softener composition and especially a rinse cycle fabric softener composition.

Good results are obtained when incorporating between 0.001-10 wt. % of fragrance precursor of the invention, drawn to the total weight of the composition, in the aqueous composition. Preferably between 0.01 and 35 wt. % and more preferably between 2 and 15 wt. % of any fabric softening active ingredient is present. A preferred cationic softener is an esterquat softener having the following structural formula:

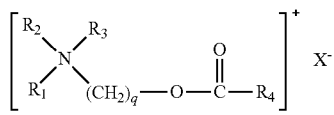

wherein R4 represents an aliphatic hydrocarbon group having from 8 to 22 carbon atoms, R2 and R3 represent $(CH_2)_s$—$R_5$ where $R_5$ represents an alkoxy carbonyl group containing from 8 to 22 carbon atoms, benzyl, phenyl, (C1-C4)-alkyl substituted phenyl, OH or H; q, s, and t, each independently, represent an integer from 1 to 3; and $X^-$ is a softener compatible anion.

The invention will be described in more detail in the following examples, which do not limit the invention, but merely illustrate the invention. Unless otherwise indicated, all percentages are by weight drawn to the weight of the final composition.

EXAMPLE 1

Figure 5A:
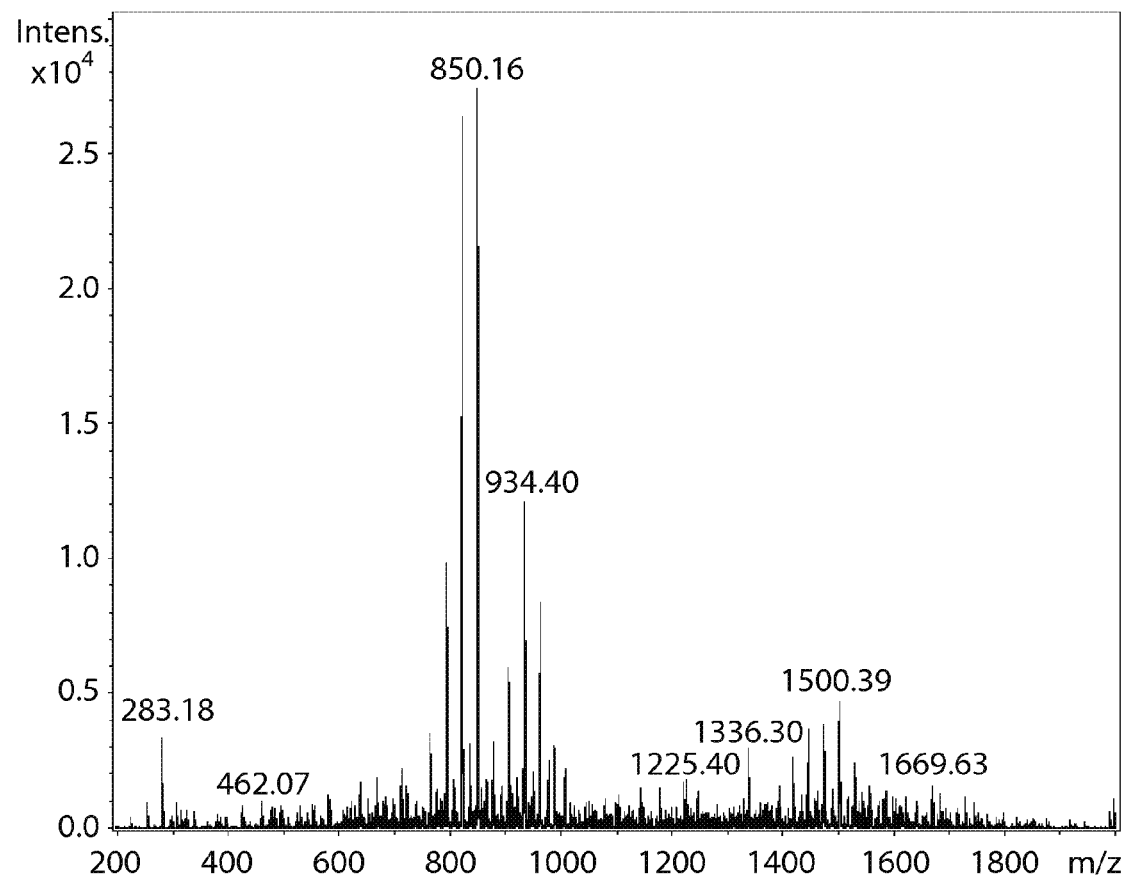
FIGS. 5a-5c show the Mass Spectrum of the reaction products of Varisoft 510 with C10 aldehyde.
Figure 5B:
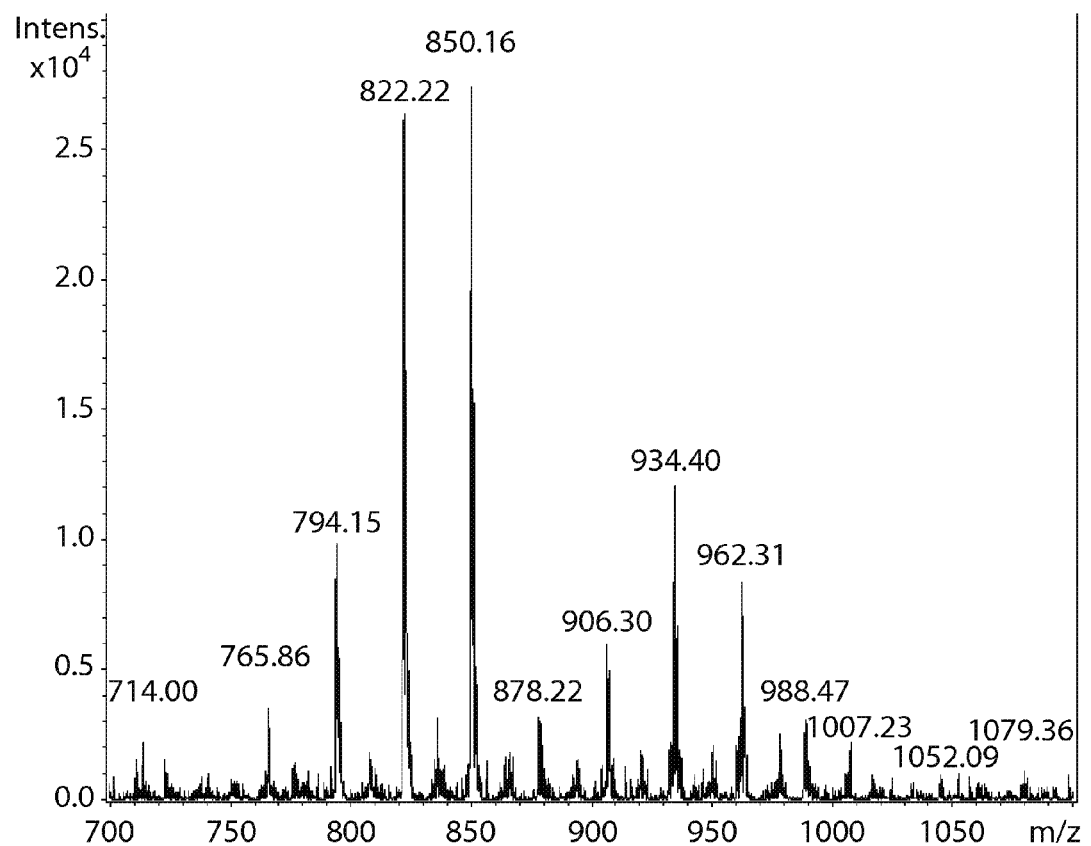
Figure 5C:
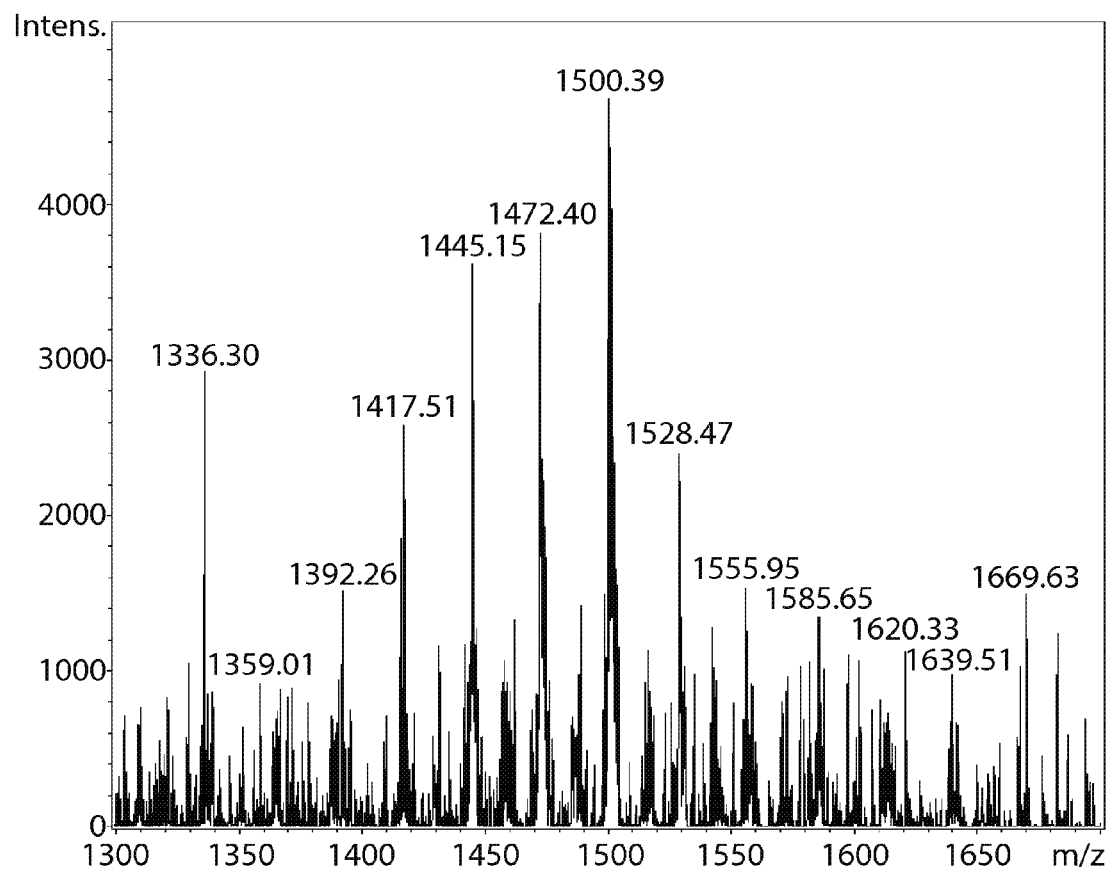

Fragrance precursors can be formed by preferable but not limited to combining Varisoft 510 (3.0 g) with decyl aldehyde (1.8 ml), water (0.2 ml) and p-toluenesulfonic acid monohydrate (20 mg). The reaction was then heated in a 60° C. oil bath with stirring overnight open to the air. The reaction was then cooled to room temperature and solidified upon standing. In FIG. 4, the proton- and $^{13}$-NMR spectra are given of Varisoft 510 and of Varisoft 510 reacted with $C_{10}$ aldehyde. FIG. 5 shows the mass spectrum of the reaction products.

Fragrance precursors can also be formed by preferable but not limited to the above reaction without the addition of water.

EXAMPLE 2

Fabric softener compositions are prepared comprising 5 wt % esterquat having the following structural formula:

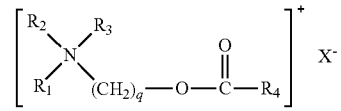

wherein R4 represents an aliphatic hydrocarbon group having from 8 to 22 carbon atoms, R2 and R3 represent $(CH_2)_s$—$R_5$ where $R_5$ represents an alkoxy carbonyl group containing from 8 to 22 carbon atoms, benzyl, phenyl, (C1-C4)-alkyl substituted phenyl, OH or H; q, s, and t, each independently, represent an integer from 1 to 3; and $X^-$ is a softener compatible anion. 1 wt % of the amido amine fragrance precursor compounds prepared; and 94 wt. % water. Fabric was treated with the fabric softener composition prepared, and the release of fragrance was measured after 1 day and after 5 days by solid phase micro extraction (SPME) coupled with GC/MS. For $C_{10}$ aldehydes the amount of fragrance released on day 1 and on day 5 is about the same. Showing the desired sustained release of fragrance from the fabric surface.

What is claimed is:

1. A fragrance precursor compound comprising one or more of the compounds derived from the reaction of X—OH and an aldehyde or ketone, said fragrance precursor compounds being of the formula X—O—C(R)(R*)(R**) wherein R is a $C_{6-24}$ alkyl group, a $C_{6-24}$ aralkyl group or a $C_{6-24}$ alkaryl group; R* is H or a $C_{6-24}$ alkyl group, a $C_{6-24}$ aralkyl group or a $C_{6-24}$ alkaryl group; R** is O—H or O—X; O—X representing a moiety derived from X—OH, and wherein X—OH is a material containing at least one hydroxyl group chosen from surfactants containing at least one hydroxyl group, fabric softener materials containing at least one hydroxyl group, softener precursor ester amines containing at least one hydroxyl group, softener precursor amido amines containing at least one hydroxyl group, hair conditioners containing at least one hydroxyl group, skin conditioners containing at least one hydroxyl group, saccharides, and polymers containing at least one hydroxyl group; wherein X—OH is of the following structure:

wherein $R_1$ is:
(a) $C_1$-$C_{22}$ alkylenecarboxy moiety having the formula: —$(CH_2)_e R_3$ wherein $R_3$ is —$NHCOR_4$; or —$OCOR_4$; or —$NR_5 COR_4$; and wherein $R_4$ and $R_5$ are each independently $C_1$-$C_{22}$ akyl or alkenyl; and e is an integer from 1 to 22; or
(b) $C_1$-$C_{22}$ linear or branched alkyl; or
(c) $C_1$-$C_{22}$ linear or branched alkenyl; or
(d) $C_2$-$C_{22}$ substituted or unsubstituted alkylenoxy; or
(e) $C_3$-$C_{22}$ substituted or unsubstituted alkylenoxy alkyl; or
(f) $C_6$-$C_{22}$ substituted or unsubstituted aryloxy; or
(g) $C_7$-$C_{22}$ substituted or unsubstituted alkylenearyl; or
(h) $C_7$-$C_{22}$ substituted or unsubstituted alkyleneoxyaryl; or
(i) $C_7$-$C_{22}$ oxyalkylenearyl; or
(j) a unit having the formula:
—$(CH_2)_y R_6$ wherein R$_6$ is —SO$_3$M, —OSO$_3$M, —PO$_3$M, —OPO$_3$M, Cl or mixtures thereof, wherein M is hydrogen, or one or more salt forming cations sufficient to satisfy charge balance, or combinations thereof;

y is an integer from 1 to about 22; and (k) a combinations of at least two of (a) through (j); and q is an integer from 0 to about 22; m is an integer from 0 to about 22; Q is (CH$_2$) or (CH$_2$CHR$_7$O); R$_7$ is independently hydrogen, methyl, ethyl, propyl or benzyl; B is H or OH; and Y is S.

2. The fragrance precursor of claim 1, wherein the aldehyde is at least one aldehyde chosen from:
(a) Phenylacetaldehyde; or
(b) p-methyl phenylacetaldehyde; or
(c) p-isopropyl phenylacetaldehyde; or
(d) methylnonyl acetaldehyde; or
(e) phenylpropanal; or
(f) 3-(4-t-butylphenyl)-2-methyl propanal; or
(g) 3-(4-t-butylphenyl)-propanal; or
(h) 3-(4-methoxyphenyl)-2-methylpropanal; or
(i) 3-(4-isopropylphenyl)-2-methylpropanal; or
(j) 3-(3,4-methylenedioxyphenyl)-2-methylpropanal; or
(k) 3-(4-ethylpheny)-2,2dimethylpropanal; or
(l) phenylbutanal; or
(m) 3-methyl-5-phenylpentanal; or
(n) hexanal; or
(o) trans-2-hexenal; or
(p) cis-hex-3-enal; or
(q) heptanal; or
(r) cis-4-heptenal; or
(s) 2-ethyl-2-heptenal; or
(t) 2,6-dimethylpropanal; or
(u) 2,4-heptadienal; or
(v) octanal; or
(w) 2-octenal; or
(x) 3,7-dimethyloctanal; or
(y) 3,7-dimethyl-2,6-octadien-1-al; or
(z) 3,7-dimethyl-1,6-octadien-3-al; or
(aa) 3,7-dimethyl-6-octenal; or
(bb) 3,7-dimethyl-7-hydroxyoctan-1-al; or
(cc) nonanal; or
(dd) 6-nonenal; or
(ee) 2,4-nonadienal; or
(ff) 2,6-nonadienal; or
(gg) decanal; or
(hh) 2-methyl decanal; or
(ii) 4-decenal; or
(jj) 9-decenal; or
(kk) 2,4-decadienal; or
(ll) undecanal; or
(mm) 2-methyldecanal; or
(nn) 2-methylundecanal; or
(oo) 2,6,10-trimethyl-9-undecenal; or
(pp) undec-10-enyl aldehyde; or
(qq) undec-8-enanal; or
(rr) dodecanal; or
(ss) tridecanal; or
(tt) tetradecanal; or
(uu) anisaldehyde; or
(vv) bourgenonal; or
(ww) cinnamic aldehyde; or
(xx) α-amylcinnam-aldehyde; or
(yy) α-hexyl cinnamaldehyde; or
(zz) methoxy cinnamaldehyde; or
(aaa) citronellal; or
(bbb) hydroxy-citronellal; or
(ccc) isocyclocitral; or
(ddd) citronellyl oxyacet-aldehyde; or
(eee) cortexaldehyde; or
(fff) cumminic aldehyde; or
(ggg) cyclamem aldehyde; or
(hhh) florhydral; or
(iii) heliotropin; or
(jjj) hydrotropic aldehyde; or
(kkk) lilial; or
(lll) vanillin; or
(mmm) ethyl vanillin; or
(nnn) benzaldehyde; or
(ooo) p-methyl benzaldehyde; or
(ppp) 3,4-dimethoxybenzaldehyde; or
(qqq) 3-and4-(4-hydroxy-4-methyl-pentyl)-3-cyclohexene-1-caroxaldehyde; or
(rrr) 2,4-dimethyl-3-cyclohexene-1-carboxaldehyde; or
(sss) 1-methyl-3-4-methylpentyl-3-cyclohexencarboxaldehyde; or
(ttt) p-methylphenoxyacetaldehyde.

3. The fragrance precursor of claim 1, wherein the ketone is at least one ketone chosen from:
(a) alpha-damascone; or
(b) beta-damascone; or
(c) delta-damascone; or
(d) beta-damascenone; or
(e) muscone; or
(f) 6,7-dihydro-1,1,2,3,3-pentamethyl-4(5H)-indanone; or
(g) cashmeran; or
(h) cis-jasmone; or
(i) dihydrojasmone; or
(j) alpha-ionone; or
(k) beta-ionone; or
(l) dihydro-beta-ionone; or
(m) gamma-methyl ionone; or
(n) alpha-iso-methyl ionone; or
(o) 4-(3,4-methylenedioxyphenyl)butan-2-one; or
(p) 4-(4-ydroxyphenyl)butan-2-one; or
(q) methyl beta-naphthyl ketone; or
(r) methyl cedryl ketone; or
(s) 6-acetyl-1,1,2,4,4,7-hexamethyltetralin (tonalid) ; or
(t) 1-carvone; or
(u) 5-cyclohexadecen-1-one; or
(v) acetophenone; or
(w) decatone; or
(x) 2[2-(4-methyl-3-cyclohexenyl-1-yl)propyl]cyclopentan-2-one; or
(y) 2-sec-butylcyclohexanone; or
(z) beta-dihydro ionone; or
(aa) allyl ionone; or
(bb) alpha-irone; or
(cc) alpha-cetone; or
(dd) alpha-irisone; or
(ee) acetanisole; or
(ff) geranyl acetone; or
(gg) 1 -(2-methl-5-isopropyl-2-cyclohexenyl)-1-propanone; or
(hh) acetyl diisoamylene; or
(ii) methyl cyclocitrone; or
(jj) 4-t-pentyl cyclohexanone; or
(kk) p-t-butylcclohexanone; or
(ll) o-t-butylcyclohexanone; or
(mm) ethyl amyl ketone; or
(nn) ethyl pentyl ketone; or
(oo) menthone; or
(pp) methyl-7,3-dihydro-2H-1,5-benzodioxepine-3-one; or (qq) fenchone; or
(rr) methyl naphthyl ketone; or
(ss) propyl naphthy ketone; and
(tt) methyl hydroxynaphthyl ketone.

4. A fragrance precursor compound delivery system comprising:
   (a) at least 0.001% by weight of the fragrance precursor compound of claim 1; and
   (b) at least one carrier.

5. A laundry detergent comprising:
   (a) at least 0.001% by weight of the fragrance precursor compound of claim 1;
   (b) at least one detersive surfactant; and
   (c) carriers and adjunct ingredients.

6. A fabric softener or fabric softening dryer sheet comprising:
   (a) at least 0.001% by weight of the fragrance precursor compound of claim 1; and
   (b) a fabric softening compound.

7. A perfume or fine fragrance comprising:
   (a) at least 0.001% by weight of the fragrance precursor compound of claim 1; and
   (b) at least 0.01% to 99% by weight of an admixture of fragrance raw materials.

8. A personal care product, or oral care product or hard surface care product comprising:
   (a) from 0.001% by weight of the fragrance precursor compound of claim 1; and
   (b) from 0.1% by weight, of a surfactant, or emollient or abrasive or anti-bacterial agent suitable for use in personal care or oral care or hard surface care products.

9. A method of preparing the fragrance precursor compound of claim 1 comprising reacting the aldehyde or ketone and X—OH.

10. The method of claim 9, wherein the reaction is acid catalyzed.

* * * * *